(12) United States Patent
Shimuta (10) Patent No.: US 10,258,762 B2
(45) Date of Patent: Apr. 16, 2019

(54) SLEEP SUPPORT APPARATUS (71) Applicant: Murata Manufacturing Co., Ltd., Nagaokakyo-shi, Kyoto-fu (JP)

(72) Inventor: Toru Shimuta, Nagaokakyo (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 213 days.

(21) Appl. No.: 15/268,687

(22) Filed: Sep. 19, 2016

(65) Prior Publication Data

US 2017/0000971 A1 Jan. 5, 2017

Related U.S. Application Data (63) Continuation of application No. PCT/JP2015/056309, filed on Mar. 4, 2015.

(30) Foreign Application Priority Data

Mar. 25, 2014 (JP) ................................. 2014-062595

(51) Int. Cl.
*A61M 21/02* (2006.01)
*A61B 5/04* (2006.01)
(Continued)

(52) U.S. Cl.
CPC .............. *A61M 21/02* (2013.01); *A61B 5/02* (2013.01); *A61B 5/0205* (2013.01);
(Continued)

(58) Field of Classification Search
CPC .......... A61M 21/02; A61M 2021/0066; A61M 2205/07; A61M 2205/3368;
(Continued)

(56) References Cited

U.S. PATENT DOCUMENTS

| 5,441,476 A | * | 8/1995 | Kitado | ................. | A61M 21/00 600/21 |
| 2006/0200011 A1 | * | 9/2006 | Suzuki | ................. | A61B 5/0205 600/301 |
| 2009/0240155 A1 | * | 9/2009 | Nakayama | ......... | A61B 5/02416 600/500 |

FOREIGN PATENT DOCUMENTS

| JP | 05-322262 A | 12/1993 |
| JP | 2005-237531 A | 9/2005 |

(Continued)

OTHER PUBLICATIONS

English translation of Official Communication issued in corresponding International Application PCT/JP2015/056309, dated Jun. 9, 2015.

*Primary Examiner* — Christine H Matthews
*Assistant Examiner* — Joshua Daryl D Lannu
(74) *Attorney, Agent, or Firm* — Keating & Bennett, LLP (57) ABSTRACT

A sleep support apparatus includes a pair of electrocardiographic electrodes that detect an electrocardiographic signal, a photoelectric pulse wave sensor that includes a light emitter and a light receiver and that detects a photoelectric pulse wave signal, peak detectors that respectively detect the peaks of the electrocardiographic signal and the photoelectric pulse wave signal, a pulse wave transit time clock that obtains a pulse wave transit time from a time difference between the peak of the photoelectric pulse wave signal and the peak of the electrocardiographic signal, a sleep state detector that determines that a user's body has not reached a state suitable for sleep when the pulse wave transit time is less than or equal to a certain threshold, and a forearm heater that increases a temperature of a forearm when it is determined the user's body has not reached a state suitable for sleep.

16 Claims, 7 Drawing Sheets (51) Int. Cl.
*A61B 5/02* (2006.01)
*A61B 5/024* (2006.01)
*A61B 5/0245* (2006.01)
*A61B 5/0205* (2006.01)
*A61B 5/021* (2006.01)
*A61B 5/00* (2006.01)
*A61M 21/00* (2006.01)

(52) U.S. Cl.
CPC ........ *A61B 5/0245* (2013.01); *A61B 5/02125* (2013.01); *A61B 5/02405* (2013.01); *A61B 5/02416* (2013.01); *A61B 5/04012* (2013.01); *A61B 5/486* (2013.01); *A61B 5/4809* (2013.01); *A61B 5/02438* (2013.01); *A61B 5/4812* (2013.01); *A61B 5/6824* (2013.01); *A61B 5/6828* (2013.01); *A61B 5/7203* (2013.01); *A61M 2021/0022* (2013.01); *A61M 2021/0066* (2013.01); *A61M 2205/07* (2013.01); *A61M 2205/3368* (2013.01); *A61M 2205/3653* (2013.01); *A61M 2205/3673* (2013.01); *A61M 2210/083* (2013.01); *A61M 2210/086* (2013.01); *A61M 2230/04* (2013.01); *A61M 2230/18* (2013.01); *A61M 2230/30* (2013.01)

(58) Field of Classification Search
CPC .. A61M 2205/3653; A61M 2205/3673; A61M 2210/083; A61M 2230/04; A61M 2230/18; A61M 2230/30; A61M 2210/086; A61M 2021/0022; A61B 5/6824; A61B 5/04012; A61B 5/0245; A61B 5/02438; A61B 5/02405; A61B 5/0205; A61B 5/02; A61B 5/6828; A61B 5/7203; A61B 5/02125; A61B 5/02416; A61B 5/4809; A61B 5/4812; A61B 5/486

See application file for complete search history.

(56) References Cited

FOREIGN PATENT DOCUMENTS

| | | |
|---|---|---|
| JP | 2006-212218 A | 8/2006 |
| JP | 2008-101307 A | 5/2008 |
| JP | 2009-022565 A | 2/2009 |
| JP | 2009-225971 A | 10/2009 |
| JP | 2010-068941 A | 4/2010 |
| JP | 2012-055464 A | 3/2012 |

* cited by examiner

SLEEP SUPPORT APPARATUS

CROSS REFERENCE TO RELATED APPLICATIONS

This application claims the benefit of priority to Japanese Patent Application 2014-062595 filed on Mar. 25, 2014 and is a Continuation Application of PCT/JP2015/056309 filed on Mar. 4, 2015. The entire contents of each of these applications are hereby incorporated by reference herein.

BACKGROUND OF THE INVENTION

1. Field of the Invention

The present invention relates to a sleep support apparatus.

2. Description of the Related Art

Technology has been proposed for detecting when a person is sleepy and for helping the person to sleep when the person is detected to be sleepy (for example, Japanese Unexamined Patent Application Publication No. 2010-68941).

Japanese Unexamined Patent Application Publication No. 2010-68941 discloses a hypnagogic system including a pulse wave sensor that obtains pulse wave data of a person riding on a vehicle, an electrocardiographic sensor that obtains heartbeat data, a hypnagogic control ECU that detects that the person is sleepy, and a plurality of on-vehicle apparatuses, such as a seat reclining apparatus, a massage apparatus, a seat air-conditioning apparatus, an air conditioner, an oxygen adding apparatus, audio equipment, a sunshade opening/closing apparatus, lighting equipment, ottoman, and a monitor screen, for performing operations suitable for the person's sleep.

In this hypnagogic system, the hypnagogic control ECU detects the person's sleepiness based on the pulse wave data detected by the pulse wave sensor and the electrocardiographic data detected by the electrocardiographic sensor, and, when the person's sleepiness is detected, causes the on-vehicle apparatuses to perform operations suitable for sleep.

A sleepy state is not necessarily the state of a body that is suitable for sleep. That is, a person who feels a chronic chill or a person who lacks sleep cannot fall asleep even when the person is very sleepy. However, the above-described technology in Japanese Unexamined Patent Application Publication No. 2010-68941 is incapable of detecting whether the body is in a state suitable for sleep, although the technology can detect whether the person is sleepy. Thus, when the person is detected to be sleepy and control is applied to the on-vehicle apparatuses to perform operations suitable for sleep, the result is that whether the person's body is in a state suitable for sleep cannot be detected.

SUMMARY OF THE INVENTION

Preferred embodiments of the present invention provide a sleep support apparatus capable of detecting whether a state of a user's body is a state suitable for sleep, and putting the user's body into a state suitable for sleep.

A sleep support apparatus according to a preferred embodiment of the present invention includes a pair of electrocardiographic electrodes that detect an electrocardiographic signal; a pulse wave sensor that detects a pulse wave signal; a peak detector that detects a peak of the electrocardiographic signal, detected by the pair of electrocardiographic electrodes, and of the pulse wave signal, detected by the pulse wave sensor; a pulse wave transit time computer that obtains a pulse wave transit time from a time difference between the peak of the pulse wave signal and the peak of the electrocardiographic signal, the peaks being detected by the peak detector; and a detector that determines that a user's body has not reached a state suitable for sleep when the pulse wave transit time obtained by the pulse wave transit time computer is less than or equal to a threshold value.

The pulse wave transit time tends to become shorter when sympathetic nerves, out of autonomic nerves, are active (dominant), such as when the user is nervous, when the user's body is tense, and when the user's blood vessels constrict and the user has poor blood circulation (that is, the body is not in a state suitable for sleep). In a sleep support apparatus according to a preferred embodiment of the present invention, a pulse wave transit time is obtained from a time difference between the peak of the pulse wave signal and the peak of the electrocardiographic signal, and it is determined that a user's body has not reached a state suitable for sleep when the pulse wave transit time is less than or equal to a threshold value. Therefore, whether the state of the user's body is a state suitable for sleep is able to be determined, and the user's body is able to be put into a state suitable for sleep.

Preferably, the sleep support apparatus according to a preferred embodiment of the present invention includes a heartbeat interval calculator that obtains a heartbeat interval from the electrocardiographic signal detected by the pair of electrocardiographic electrodes. Preferably, the threshold value is set to become smaller as the heartbeat interval becomes longer, and the detector determines that the user's body has not reached a state suitable for sleep when the pulse wave transit time is less than or equal to a threshold value corresponding to the heartbeat interval obtained by the heartbeat interval calculator.

There is a corresponding relationship between the length of the heartbeat interval and the level of sleepiness. That is, the state where the pulse wave transit time is short and the heartbeat interval is short is estimated to be a state not suitable for sleep. In contrast, the state in which the pulse wave transit time is long and the heartbeat interval is long is estimated to be a state suitable for sleep. In the sleep support apparatus according to a preferred embodiment of the present invention, the threshold for determining whether the state of the body is a state suitable for sleep is set to become smaller as the heartbeat interval becomes longer. That is, the threshold value is set in accordance with the combination of the pulse wave transit time and the heartbeat interval. Therefore, whether the state of the body is a state suitable for sleep is able to be more accurately determined.

In a sleep support apparatus according to a preferred embodiment of the present invention, the threshold value is preferably set based on a maximum value of the pulse wave transit time during sleep.

The pulse wave transit time tends to gradually become shorter after the user wakes up and recover, i.e., become longer, when the user sleeps. In a sleep support apparatus according to a preferred embodiment of the present invention, the threshold value is set based on the maximum value of the pulse wave transit time during sleep, that is, the pulse wave transit time that has not been reduced by daytime activities. Therefore, the threshold for determining whether the user's body has reached a state suitable for sleep is able to be appropriately set.

In a sleep support apparatus according to a preferred embodiment of the present invention, a photoelectric pulse wave sensor that includes a light emitter and a light receiver, and that detects a photoelectric pulse wave signal is preferably used as the pulse wave sensor.

A sleep support apparatus according to a preferred embodiment of the present invention includes a first pulse wave sensor and a second pulse wave sensor that detect a pulse wave signal; a peak detector that detects a peak of a first pulse wave signal, detected by the first pulse wave sensor, and of a second pulse wave signal, detected by the second pulse wave sensor; a pulse wave transit time computer that obtains a pulse wave transit time from a time difference between the peak of the first pulse wave signal and the peak of the second pulse wave signal, the peaks being detected by the peak detector; and a detector that determines that a user's body has not reached a state suitable for sleep when the pulse wave transit time obtained by the pulse wave transit time computer is less than or equal to a threshold value.

In a sleep support apparatus according to a preferred embodiment of the present invention, a pulse wave transit time is obtained from a time difference between the peak of the first pulse wave signal and the peak of the second pulse wave signal, and it is determined that a user's body has not reached a state suitable for sleep when the pulse wave transit time is less than or equal to a threshold value. Therefore, whether the state of the user's body is a state suitable for sleep is able to be determined, and the user's body is able to be put into a state suitable for sleep.

The term "pulse wave transit time" refers to two cases: one case where the term refers to a time taken by a pulse wave to propagate between two certain portions of a body; and the other case where the term refers to a time difference between the peak of an electrocardiographic signal and the peak of a pulse wave signal. In the present specification, the term "pulse wave transit time" is used to express these two meanings and covers the two cases described above.

Preferably, a sleep support apparatus according to a preferred embodiment of the present invention includes a pulse interval calculator that obtains a pulse interval from the first pulse wave signal or the second pulse wave signal. Preferably, the threshold value is set to become smaller as the pulse interval becomes longer, and the detector determines that the user's body has not reached a state suitable for sleep when the pulse wave transit time is less than or equal to a threshold value corresponding to the pulse interval obtained by the pulse interval calculator.

There is a corresponding relationship between the length of the pulse interval and the level of sleepiness. That is, the state where the pulse wave transit time is short and the pulse interval is short is estimated as a state not suitable for sleep. In contrast, the state in which the pulse wave transit time is long and the pulse interval is long is estimated as a state suitable for sleep. In a sleep support apparatus according to a preferred embodiment of the present invention, the threshold for determining whether the state of the body is a state suitable for sleep is set to become smaller as the pulse interval becomes longer. That is, the threshold value is set in accordance with the combination of the pulse wave transit time and the pulse interval. Therefore, whether the state of the body is a state suitable for sleep is able to be more accurately determined.

In a sleep support apparatus according to a preferred embodiment of the present invention, the threshold value is preferably set based on a maximum value of the pulse wave transit time during sleep.

In a sleep support apparatus according to a preferred embodiment of the present invention, the threshold value is set based on the maximum value of the pulse wave transit time during sleep, that is, the pulse wave transit time that has not been reduced by daytime activities. Therefore, the threshold for determining whether the user's body has reached a state suitable for sleep is able to be appropriately set.

In a sleep support apparatus according to a preferred embodiment of the present invention, photoelectric pulse wave sensors, each of which includes a light emitter and a light receiver, and detect a photoelectric pulse wave signal, are preferably used as the first pulse wave sensor and the second pulse wave sensors.

Preferably, a sleep support apparatus according to a preferred embodiment of the present invention further includes a forearm heater that increases a temperature of a forearm when the detector determines that the user's body has not reached a state suitable for sleep.

When the user's fingers are cold and the peripheral vessels constrict, it is difficult for the user to sleep soundly or fall asleep, and it is also difficult for the user to sleep well. In a sleep support apparatus according to a preferred embodiment of the present invention, the temperature of the forearms is increased when the user's body has not reached a state suitable for sleep. In doing so, only the forearms can be heated without increasing the temperature of the trunk. Therefore, the state becomes such that the forearms are heated to dilate the peripheral vessels of the fingers, but the temperature of the trunk is low, which is, thus, a state suitable for sleep. As a result, the user is able to easily fall asleep and sleep well.

Preferably, a sleep support apparatus according to a preferred embodiment of the present invention further includes a leg heater that increases a temperature of a leg when the detectors determines that the user's body has not reached a state suitable for sleep.

When the user's feet are cold and the peripheral vessels constrict, it is difficult for the user to sleep soundly or fall asleep, and it is also difficult for the user to sleep well. In a sleep support apparatus according to a preferred embodiment of the present invention, the temperature of the legs is increased when the user's body has not reached a state suitable for sleep. In doing so, only the legs can be heated without increasing the temperature of the trunk. Therefore, the state becomes such that the legs are heated to dilate the peripheral vessels of the feet, but the temperature of the trunk is low, which is, thus, a state suitable for sleep. As a result, the user is able to easily fall asleep and is able to sleep well.

Preferably, a sleep support apparatus according to a preferred embodiment of the present invention further includes a neck cooler that reduces a temperature of a neck when the detector determines that the user's body has not reached a state suitable for sleep.

The user easily wakes up when the user's head becomes hot during sleep. In the sleep support apparatus according to a preferred embodiment of the present invention, the temperature of the neck is reduced when it is determined that the user's body has not reached a state suitable for sleep. In doing so, the temperature of blood flowing to the head is lowered, thus reducing the temperature of the head and putting the user's body into a state suitable for sleep. As a result, the user is able to easily fall asleep and sleep well.

According to various preferred embodiments of the present invention, whether the state of the user's body is a state suitable for sleep is able to be determined, and the user's body is able to be put into a state suitable for sleep.

The above and other elements, features, steps, characteristics and advantages of the present invention will become more apparent from the following detailed description of the preferred embodiments with reference to the attached drawings.

DETAILED DESCRIPTION OF THE PREFERRED EMBODIMENTS

Hereinafter, preferred embodiments of the present invention will be described with reference to the drawings. In the drawings, the same symbols are used for the same or corresponding portions. In the drawings, the same symbols are provided for the same elements, and overlapping descriptions are omitted.

Figure 1:
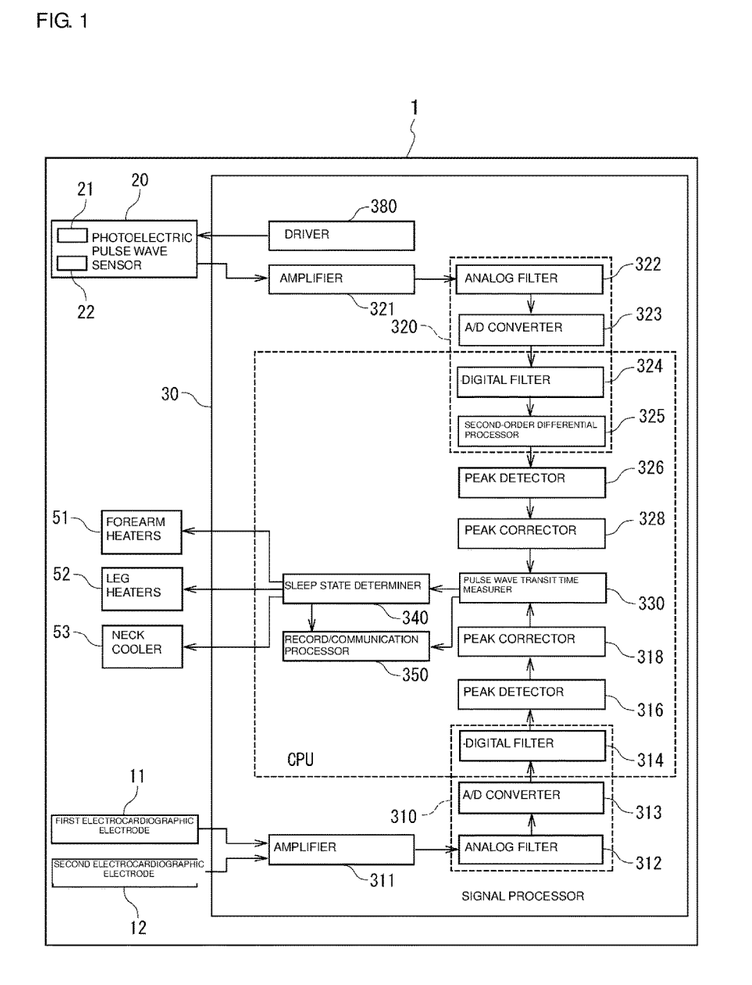
FIG. 1 is a block diagram illustrating the configuration of a sleep support apparatus according to a preferred embodiment of the present invention.
Figure 2:
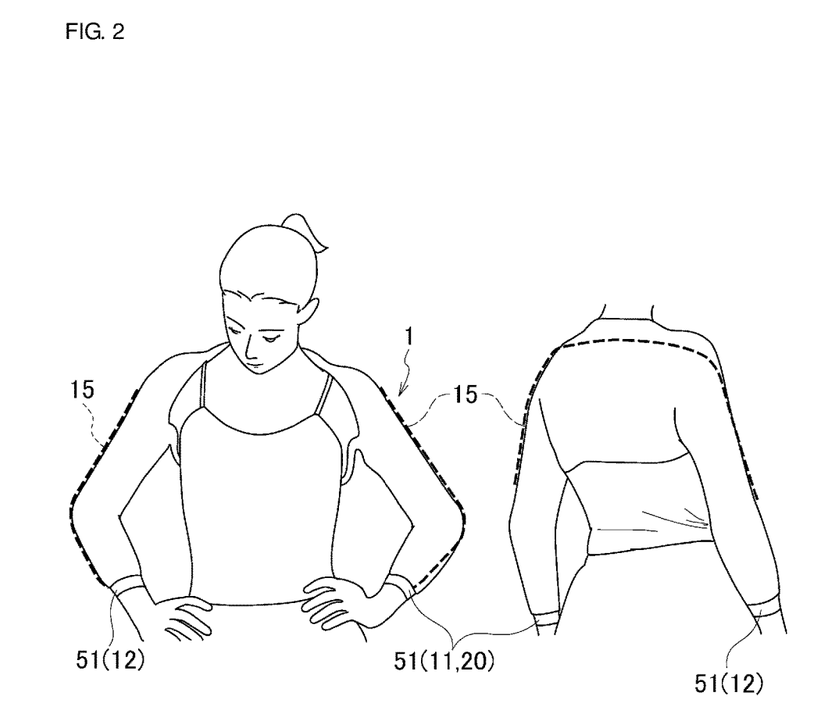
FIG. 2 is a diagram illustrating the external appearance of the sleep support apparatus according to a preferred embodiment of the present invention.

Referring to FIGS. 1 and 2, the configuration of a sleep support apparatus 1 according to a preferred embodiment of the present invention will be described. FIG. 1 is a block diagram illustrating the configuration of the sleep support apparatus 1. FIG. 2 is a diagram illustrating the external appearance of the sleep support apparatus 1.

The sleep support apparatus 1 detects an electrocardiographic signal and a photoelectric pulse wave signal, measures a pulse wave transit time from a time difference between the R-wave peak of the detected electrocardiographic signal (electrocardiographic wave) and the peak (rising point) of the photoelectric pulse wave signal (pulse wave), and determines whether the state of the user's body is a state suitable for sleep based on the measured pulse wave transit time. The sleep support apparatus 1 additionally puts the user's body into a state suitable for sleep when the sleep support apparatus 1 determines that the state of the user's body is not a state suitable for sleep.

Therefore, the sleep support apparatus 1 includes a pair of electrocardiographic electrodes (a first electrocardiographic electrode 11 and a second electrocardiographic electrode 12) that detect an electrocardiographic signal, a photoelectric pulse wave sensor that detect a photoelectric pulse wave signal, a signal processor 30 that measures the pulse wave transit time or other suitable values from the detected electrocardiographic signal and photoelectric pulse wave signal and determines whether the body state is a state suitable for sleep, and forearm heaters 51, leg heaters 52, and a neck cooler 53 that put the body into a state suitable for sleep. These elements will be described in detail below.

As illustrated in FIG. 2, the sleep support apparatus includes, for example, the first electrocardiographic electrode 11, the second electrocardiographic electrode 12, and the photoelectric pulse wave sensor 20, which are mounted on highly-elastic fabric designed and configured to be wearable continuously from the tips of the arms to the shoulders and to the back. Fabric for the trunk, which is unnecessary for measurement or wiring, may be omitted.

Preferably, when the user wears the sleep support apparatus 1, the first electrocardiographic electrode 11 is mounted to contact with any portion, such as the left wrist in the present preferred embodiment, from the fingertip of one arm, such as the left arm, to the shoulder, and the second electrocardiographic electrode 12 is mounted to contact with any portion, such as right wrist, from the fingertip of the other arm, such as the right arm, to the shoulder. A wiring cable 15, which is connected to the first electrocardiographic electrode 11 and the second electrocardiographic electrode 12, is mounted and wired on the fabric so as to lie along the surface of the user's body. Alternatively, the first and second electrocardiographic electrodes 11 and 12 may be arranged at two positions beneath the chest or neck portion of the clothes that are made from a highly-elastic material and that fit the body.

For example, conductive fabrics are preferably used as the first electrocardiographic electrode 11 and the second electrocardiographic electrode 12. Alternatively, metal (corrosion-resistive and allergy-free metal such as stainless, Au, or the like is preferable), conductive gel, or conductive rubber, for example, may be used as the first electrocardiographic electrode 11 and the second electrocardiographic electrode 12. Besides those described above, capacitive coupling electrodes whose metal surface is coated with an insulating layer, for example, may be used as the first electrocardiographic electrode 11 and the second electrocardiographic electrode 12. Each of the first electrocardiographic electrode 11 and the second electrocardiographic electrode 12 is connected to the signal processor 30 with the wiring cable 15 interposed therebetween, and outputs an electrocardiographic signal to the signal processor 30 via the wiring cable 15.

The photoelectric pulse wave sensor 20 is a sensor that optically detects a photoelectric pulse wave signal using the light absorption characteristics of blood hemoglobin. Therefore, the photoelectric pulse wave sensor 20 includes a light emitter 21 and a light receiver 22. In this case, the photoelectric pulse wave sensor 20 is preferably mounted while being in contact with any portion, such as a finger, a wrist, a forearm, an upper arm, or a shoulder, from the fingertip of a hand to a shoulder. In the present preferred embodiment, the photoelectric pulse wave sensor 20 is placed on the left wrist, that is, near the first electrocardiographic electrode 11, for example, the photoelectric pulse wave sensor 20 and the first electrocardiographic electrode 11 are placed in line or are integrated with each other.

The light emitter 21 emits light in response to a pulsed drive signal output from a driver 380 of the signal processor 30. For example, an LED, a VCSEL (Vertical Cavity Surface Emitting LASER), or a resonator-type LED may preferably be used as the light emitter 21. The driver 380 generates and outputs a pulsed drive signal to drive the light emitter 21.

The light receiver 22 outputs a detection signal in accordance with the intensity of light emitted by the light emitter 21, which passes through a human body, such as a wrist, or which is reflected from a human body, and which enters the light receiver 22. For example, a photodiode or a phototransistor is preferably used as the light receiver 22. In the present preferred embodiment, a photodiode is used as the light receiver 22. The light receiver 22 is connected to the signal processor 30, and a detection signal (photoelectric pulse wave signal) obtained by the light receiver 22 is output to the signal processor 30.

As has been described above, the first electrocardiographic electrode 11, the second electrocardiographic electrode 12, and the photoelectric pulse wave sensor 20 are each connected to the signal processor 30, and a detected electrocardiographic signal and a detected photoelectric pulse wave signal are input to the signal processor 30.

The signal processor 30 processes the input electrocardiographic signal, and measures the heart rate, heartbeat interval, and other values. The signal processor 30 processes the input photoelectric pulse wave signal, and measures the pulse rate, pulse interval, and other values. The signal processor 30 further measures a pulse wave transit time, for example, from a time difference between the R-wave peak of the detected electrocardiographic signal (electrocardiographic wave) and the peak (rising point) of the detected photoelectric pulse wave signal (or an acceleration pulse wave signal) (see FIG. 3). Based on the measured pulse wave transit time, the signal processor 30 determines whether the state of the user's body is a state suitable for sleep. When the signal processor 30 determines that the user's body has not reached a state suitable for sleep, the signal processor 30 puts the user's body into a state suitable for sleep.

To do so, the signal processor 30 is configured or programmed to include amplifiers 311 and 321, a first signal processor 310, a second signal processor 320, peak detectors 316 and 326, peak correctors 318 and 328, a pulse wave transit time clock 330, a sleep state detector 340, and a record/communication processor 350. The first signal processor 310 includes an analog filter 312, an A/D converter 313, and a digital filter 314. The second signal processor 320 includes an analog filter 322, an A/D converter 323, a digital filter 324, and a second-order differential processor 325.

Among the above-described elements, the digital filters 314 and 324, the second-order differential processor 325, the peak detectors 316 and 326, the peak correctors 318 and 328, the pulse wave transit time clock 330, the sleep state detector 340, and the record/communication processor 350 are preferably defined by a CPU that performs arithmetic operation processes, a ROM that stores programs and data that cause the CPU to execute the processes, a RAM that temporarily stores various types of data, such as the arithmetic operation results, and other data. That is, the functions of the above-described elements are achieved by executing, by the CPU, the programs stored in the ROM.

The amplifier 311 preferably includes an operational amplifier, for example, and amplifies an electrocardiographic signal detected by the first electrocardiographic electrode 11 and the second electrocardiographic electrode 12. The electrocardiographic signal amplified by the amplifier 311 is output to the first signal processor 310. Similarly, the amplifier 321 preferably includes an operational amplifier, for example, and amplifies a photoelectric pulse wave signal detected by the photoelectric pulse wave sensor 20. The photoelectric pulse wave signal amplified by the amplifier 321 is output to the second signal processor 320.

The first signal processor 310 includes the analog filter 312, the A/D converter 313, and the digital filter 314, as described above, and extracts a pulsatile component by filtering the electrocardiographic signal amplified by the amplifier 311.

The second signal processor 320 includes the analog filter 322, the A/D converter 323, the digital filter 324, and the second-order differential processor 325, as described above, and extracts a pulsatile component by filtering and applying second-order differential processing to the photoelectric pulse wave signal amplified by the amplifier 321.

The analog filters 312 and 322 and the digital filters 314 and 324 remove components, i.e., noise, other than frequencies that characterize the electrocardiographic signal and the photoelectric pulse wave signal, and perform filtering to improve S/N. More specifically, generally, frequency components from about 0.1 Hz to about 200 Hz are dominant in electrocardiographic signals, and frequency components from about 0.1 Hz to about dozens of Hz are dominant in photoelectric pulse wave signals. Thus, analog filters and digital filters, such as low-pass filters and band-pass filters, are used to filter these signals, thereby only allowing signals within the above-described frequency ranges to pass and, accordingly, improving S/N.

If the purpose is to only extract a pulsatile component, that is, if it is not necessary to obtain the electrocardiographic waveform, for example, the passband frequency range may be further narrowed to improve noise resistance, thereby blocking components other than the pulsatile component. It is not necessary to include both of the analog filters 312 and 322 and the digital filters 314 and 324, and only the analog filters 312 and 322 or only the digital filters 314 and 324 may be provided. The electrocardiographic signal, which has been filtered by the analog filter 312 and the digital filter 314, is output to the peak detector 316. Similarly, the photoelectric pulse wave signal, which has been filtered by the analog filter 322 and the digital filter 324, is output to the second-order differential processor 325.

The second-order differential processor 325 obtains a second-order differential pulse wave, i.e., an acceleration pulse wave, signal by performing second-order differential of the photoelectric pulse wave signal. The obtained acceleration pulse wave signal is output to the peak detector 326. Since the peak (rising point) of a photoelectric pulse wave is sometimes an unclear change and is, thus, difficult to detect, it is preferable to convert the photoelectric pulse wave to an acceleration pulse wave and detect the peak thereof. However, it is not essential to provide the second-order differential processor 325, and the second-order differential processor 325 may be omitted.

The peak detector 316 detects the peak (R-wave) of the electrocardiographic signal, which has been subjected to signal processing, from which the pulsatile component has been extracted, by the first signal processor 310.

In contrast, the peak detector 326 detects the peak (rising point) of the photoelectric pulse wave signal (or the acceleration pulse wave), which has been filtered by the second signal processor 320. That is, the peak detectors 316 and 326 function as the peak detector recited in the claims.

The peak corrector 318 obtains a delay time of the electrocardiographic signal in the first signal processor 310 (the analog filter 312 and the digital filter 314). Based on the obtained delay time of the electrocardiographic signal, the peak corrector 318 corrects the peak of the electrocardiographic signal, detected by the peak detector 316. Similarly, the peak corrector 328 obtains a delay time of the photoelectric pulse wave signal in the second signal processor 320 (the analog filter 322, the digital filter 324, and the second-order differential processor 325). Based on the obtained delay time of the photoelectric pulse wave signal, the peak corrector 328 corrects the peak of the photoelectric pulse wave signal (or the acceleration pulse wave signal), detected by the peak detector 326. The corrected peak of the electrocardiographic signal and the corrected peak of the photoelectric pulse wave (or the acceleration pulse wave) are output to the pulse wave transit time clock 330. When it is determined that the delay time of the electrocardiographic signal is the same or substantially the same as the delay time of the photoelectric pulse wave signal, it is not essential to provide the peak corrector 318, and the peak corrector 318 may be omitted.

Figure 3:
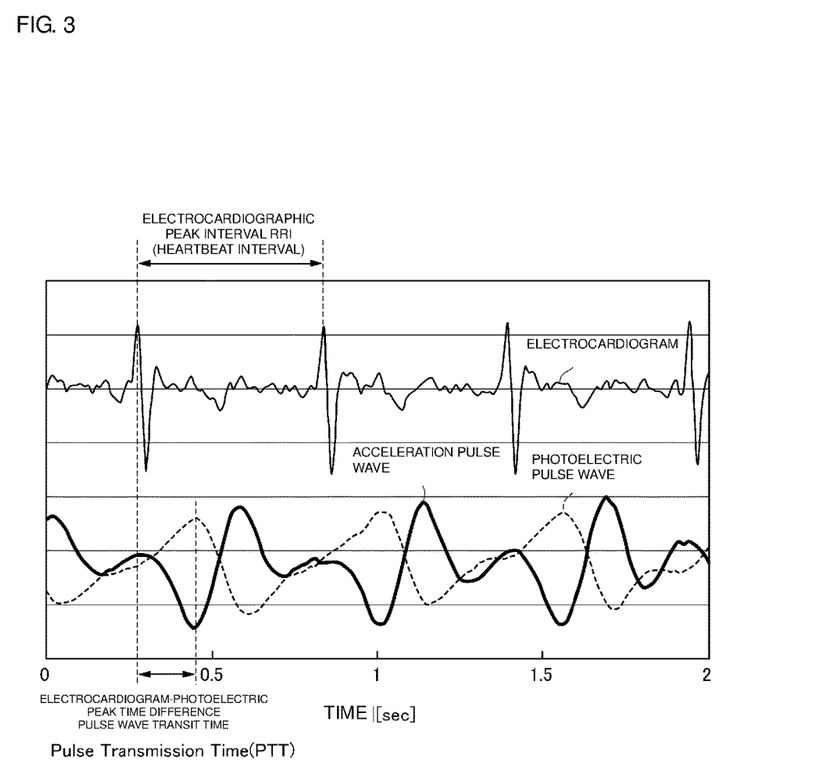
FIG. 3 is a diagram illustrating an electrocardiographic waveform, a photoelectric pulse waveform, and a pulse wave transit time.

The pulse wave transit time clock 330 obtains a pulse wave transit time from an interval (time difference) between the R-wave (peak) of the electrocardiographic signal, corrected by the peak corrector 318, and the peak (rising time) of the photoelectric pulse wave signal (or the acceleration pulse wave), corrected by the peak corrector 328. That is, the pulse wave transit time clock 330 functions as the pulse wave transit time computer recited in the claims. In this case, FIG. 3 illustrates the pulse wave transit time obtained from the interval between the R-wave (peak) of the electrocardiographic signal and the peak of the photoelectric pulse wave signal (acceleration pulse wave). In FIG. 3, the waveform of the electrocardiographic signal is indicated by a thin solid line, and the photoelectric pulse wave signal is indicated by a broken line. In addition, the waveform of the acceleration pulse wave is indicated by a thick bold line.

Note that the pulse wave transit time clock 330 calculates the heart rate, heartbeat interval, and other values from the electrocardiographic signal, in addition to the pulse wave transit time. That is, the pulse wave transit time clock 330 also functions as the heartbeat interval calculator recited in the claims. Similarly, the pulse wave transit time clock 330 additionally calculates the pulse rate, pulse interval, and other values from the photoelectric pulse wave signal (acceleration pulse wave). Measurement data, such as the calculated pulse wave transit time, heart rate, heartbeat interval, pulse rate, pulse interval, and acceleration pulse wave, are output to the sleep state detector 340 and the record/communication processor 350.

The sleep state detector 340 determines that the user's body has not reached a state suitable for sleep when the pulse wave transit time obtained by the pulse wave transit time clock 330 is less than or equal to a certain threshold. That is, the sleep state detector 340 functions as a detector recited in the claims. In this case, the above-mentioned threshold value is set to be smaller when the heartbeat interval becomes longer (see the broken line in FIG. 4). Therefore, the sleep state detector 340 determines that the user's body has not reached a state suitable for sleep when the pulse wave transit time is less than or equal to a threshold value corresponding to the heartbeat interval, that is, when the combination of the heartbeat interval (PRI) and the pulse wave transit time is not in an area (an upper area above the broken line in FIG. 4) suitable for sleep.

Figure 4:
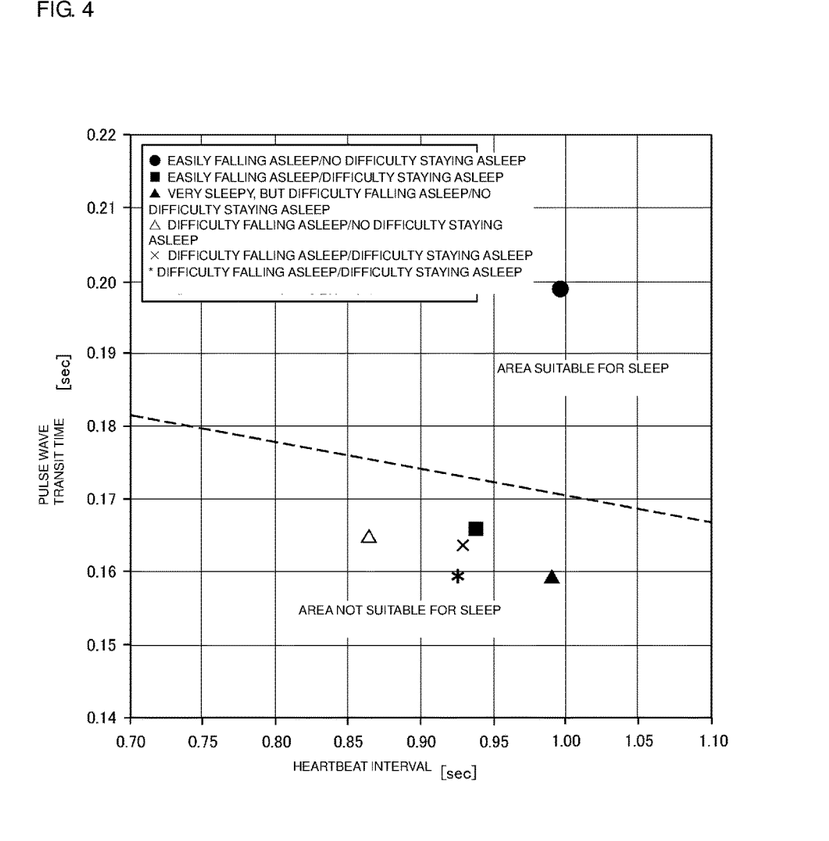
FIG. 4 is a diagram illustrating an example of an area suitable for sleep and an area not suitable for sleep, determined in accordance with the pulse wave transit time and the heartbeat interval.

In this case, FIG. 4 is a diagram illustrating an example of an area suitable for sleep and an area not suitable for sleep, determined in accordance with the pulse wave transit time and the heartbeat interval. The heartbeat interval (sec) is plotted on the abscissa, and the pulse wave transit time (sec) is plotted on the ordinate in FIG. 4. The pulse wave transit time tends to become shorter when sympathetic nerves, out of autonomic nerves, are active (dominant), such as when the user is nervous, when the user's body is tense, and when the user's blood vessels constrict and the user has poor blood circulation (that is, the body is not in a state suitable for sleep). There is also a corresponding relationship between the length of the heartbeat interval and the level of sleepiness. Thus, the state where the pulse wave transit time is short and the heartbeat interval is short (the lower area below the broken line in FIG. 4) is determined as a state not suitable for sleep. In contrast, the state in which the pulse wave transit time is long and the heartbeat interval is long (the upper area above the broken line in FIG. 4) is determined as a state suitable for sleep.

Figure 5:
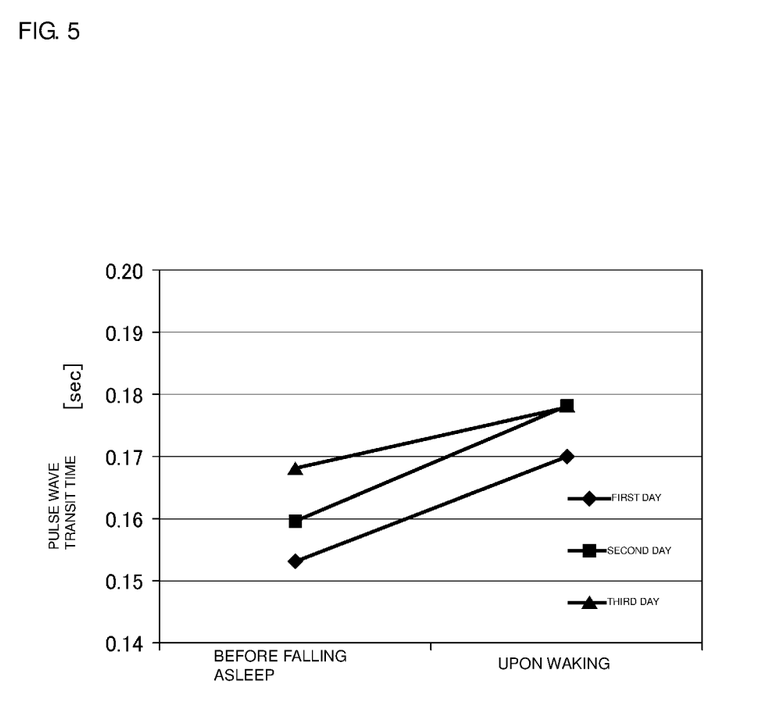
FIG. 5 is a diagram illustrating an example of changes in the pulse wave transit time before and after the user sleeps.

The threshold value, which is indicated as the broken line defining the two areas in FIG. 4, is determined using, as a determination reference value, the maximum value of the pulse wave transit time during sleep or the pulse wave transit time immediately before the user wakes up. The determination reference value is preferably updated as required in accordance with the pulse wave transit time (measurement value) while the user sleeps. In this case, the pulse wave transit time gradually becomes shorter after the user wakes up and recovers or becomes longer when the user sleeps, as illustrated in FIG. 5. Therefore, the pulse wave transit time often reaches a maximum during sleep, and particularly immediately before the user wakes up. Therefore, the pulse wave transit time is sequentially measured, and, when the measured value exceeds a present maximum value, the maximum value is updated. The determination reference value is defined in accordance with the maximum value of the obtained pulse wave transit time, or the pulse wave transit time immediately before the user wakes up. The determination reference value is tilted in accordance with the heartbeat interval, so as to set the threshold value indicated by the broken line in FIG. 4 described above.

Alternatively, the sleep state detector 340 may determine that the user's body has not reached a state suitable for sleep when the pulse wave transit time is less than or equal to a constant threshold value, regardless of the heartbeat interval. In such a case, for example, the determination reference value (the maximum value of the pulse wave transit time or the pulse wave transit time immediately before the user wakes up) is able to be used as a threshold value.

When the sleep state detector 340 determines that the user's body has not reached a state suitable for sleep, the forearm heaters 51 heat the forearms, preferably including a portion of the forearms, such as the wrists, or enhance the thermal effect, so as to increase the temperature of the forearms.

More specifically, for example, wristbands, bracelets, a shirt, or a sleepwear with a heating function is preferably used as the forearm heaters 51. In the present preferred embodiment, wristband-shaped heaters are preferably used, as illustrated in FIG. 2. The forearm heaters 51 heat the forearms or enhance the thermal effect when it is determined that the user's body has not reached a state suitable for sleep. In that case, the forearm heaters 51 adjust their output so that the temperature of the forearms becomes higher as the deviation between the pulse wave transit time and the threshold value increases. In contrast, the forearm heaters 51 maintain the temperature or reduce the degree of heating when it is determined that the state of the user's body has become a state suitable for sleep.

Non-limiting examples of a heating method used by the forearm heaters 51 include a method using an electric heater or other suitable heating device, and a method that enhances the thermal effect by tightening the cuffs, which are made of a material with a high heat-retention effect. Techniques for changing the degree of tightening the cuffs include, for example, one that changes cuff pressure using an air pump, or a mechanical tightening device. Heating may preferably be performed by restricting the temperature adjustment or providing a temperature sensor that performs feedback control such that the user will not be uncomfortable.

When the sleep state detector 340 determines that the user's body has not reached a state suitable for sleep, the leg heaters 52 heat the legs, preferably including a portion of the legs, such as the ankles, or enhance the thermal effect of the legs, so as to increase the temperature of the legs.

More specifically, for example, socks, leg warmers, or a sleepwear with a heating function may preferably be used as the leg heaters 52. The leg heaters 52 heat the legs or enhance the thermal effect when it is determined that the user's body has not reached a state suitable for sleep. The leg heaters 52 adjust their output so that the temperature of the legs increases as the deviation between the pulse wave transit time and the threshold value increases. In contrast, the leg heaters 52 maintain the temperature or weaken the degree of heating when it is determined that the state of the user's body has become a state suitable for sleep. Techniques similar to those used by the forearm heaters 51 may preferably be used as a heating method for the leg heaters 52.

The neck cooler 53 reduces the temperature of the neck by cooling the neck when the sleep state detector 340 determines that the user's body has not reached a state suitable for sleep.

More specifically, for example, a neckband, a shirt, or a sleepwear with a cooling function may preferably be used as the neck cooler 53. The neck cooler 53 cools the neck or enhances the heat dissipation effect when it is determined that the user's body has not reached a state suitable for sleep. The neck cooler 53 adjusts its output so that the temperature of the neck is reduced as the deviation between the pulse wave transit time and the above-mentioned threshold increases. In contrast, the neck cooler 53 maintains the temperature or weakens the degree of cooling when it is determined that the state of the user's body has become a state suitable for sleep.

Non-limiting examples of a cooling method used by the neck cooler 53 include a method of blowing air using a piezoelectric pump, a method that uses a Peltier device, and a method that enhances the heat dissipation effect by loosening the collar. Techniques for changing the degree of tightening the collar include, for example, one that uses an air pump, or a mechanical device. Cooling may preferably be done by restricting the temperature adjustment or providing a temperature sensor for performing feedback control so that the user will not be uncomfortable.

Note that the forearm heaters 51, the leg heaters 52, and the neck cooler 53 described above may be appropriately combined and used together or may be separately and individually used. When the sleep support apparatus is defined by clothes, it is preferable for the sleep support apparatus 1 to include the forearm heaters 51, the leg heaters 52, and the neck cooler 53 as elements that are removable from the clothes.

Figure 6:
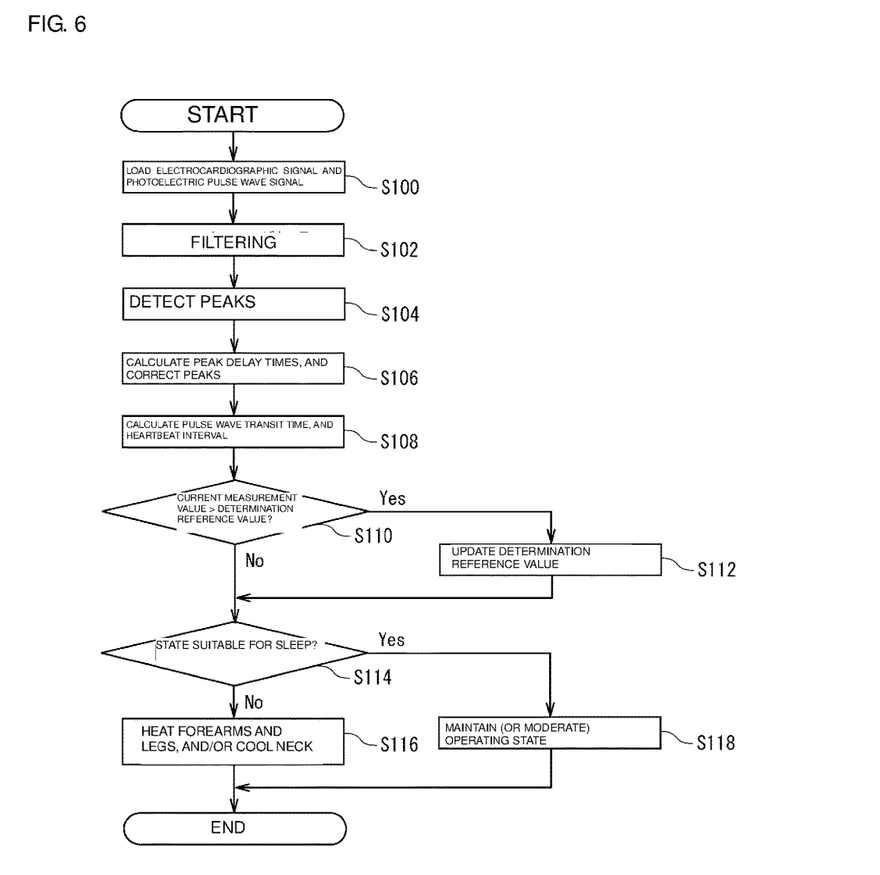
FIG. 6 is a flowchart illustrating the procedure of a sleep support process performed by the sleep support apparatus according to another preferred embodiment of the present invention.

Referring to FIG. 6, the operation of the sleep support apparatus 1 will be described. FIG. 6 is a flowchart illustrating the procedure of a sleep support process performed by the sleep support apparatus 1. The process illustrated in FIG. 6 is executed primarily by the signal processor 30.

In step S100, an electrocardiographic signal (electrocardiographic waveform) detected by the pair of electrocardiographic electrodes 11 and 12 and a photoelectric pulse wave signal (photoelectric pulse waveform) detected by the photoelectric pulse wave sensor 20 are loaded. Thereafter, in step S102, the electrocardiographic signal and the photoelectric pulse wave signal, which are loaded in step S100, are subjected to filtering. The photoelectric pulse wave signal is additionally subjected to second-order differential processing, so as to obtain an acceleration pulse wave.

Next in step S104, the peaks of the electrocardiographic signal and the photoelectric pulse wave signal (acceleration pulse wave signal) are detected.

Thereafter in step S106, the delay time (shift amount) of each of the R-wave peak of the electrocardiographic signal and the peak of the photoelectric pulse wave signal (acceleration pulse wave) is obtained, and, based on the obtained delay times, the R-wave peak of the electrocardiographic signal and the peak of the photoelectric pulse wave signal (acceleration pulse wave) are corrected. Note that the method of correcting each peak is as described above, and a detailed description thereof is omitted here.

In step S108, a pulse wave transit time is calculated from the time difference between the corrected peak of the photoelectric pulse wave signal (acceleration pulse wave) and the corrected R-wave peak of the electrocardiographic signal. A heartbeat interval is obtained from the electrocardiographic signal.

Next in step S110, it is determined whether the pulse wave transit time (current measurement value), calculated in step S108, is greater than the currently stored determination reference value (maximum value of the pulse wave transit time). When the pulse wave transit time (current measurement value) is greater than the currently stored determination reference value, the process proceeds to step S112. In contrast, when the pulse wave transit time (current measurement value) is less than or equal to the currently stored determination reference value, the process proceeds to step S114.

In step S112, the determination reference value (the maximum value of the pulse wave transit time) is updated. That is, the pulse wave transit time (current measurement value) obtained in step S108 is stored as a new determination reference value. Based on the new determination reference value, a threshold value (see the broken line in FIG. 4) used to determine whether the state is a state suitable for sleep is reset. Thereafter, the process proceeds to step S114.

In step S114, it is determined whether the pulse wave transit time is longer than a threshold value corresponding to the heartbeat interval, that is, whether the state of the user's body is a state suitable for sleep, i.e., whether the state is within an area suitable for sleep in FIG. 4. When the pulse wave transit time is longer than a threshold value corresponding to the heartbeat interval, that is, when the state of the user's body has become a state suitable for sleep, the process proceeds to step S118. In contrast, when the pulse wave transit time is less than or equal to a threshold value corresponding to the heartbeat interval, that is, when the state of the user's body is not a state suitable for sleep, the process proceeds to step S116.

In step S116, the temperature of the forearms, such as the wrists, is increased by heating the forearms or by enhancing the thermal effect of the forearms. Similarly, the temperature of the legs, such as the ankles, is increased by heating the legs or by enhancing the thermal effect of the legs. Furthermore, the temperature of the neck is reduced by cooling the neck. Therefore, the state of the user's body becomes a state suitable for sleep. Thereafter, the process exits from the main process.

In contrast, in step S118, the operating state of the forearm heaters 51, the leg heaters 52, and the neck cooler 53 is maintained without being changed or is moderated, and the state of the user's body is maintained as a state suitable for sleep. Thereafter, the process exits from the main process.

As has been described above, according to the present preferred embodiment, the pulse wave transit time is obtained from the time difference between the peak of the photoelectric pulse wave signal and the peak of the electrocardiographic signal, and it is determined that the user's body has not reached a state suitable for sleep when the pulse wave transit time is less than or equal to the threshold value. Accordingly, whether the state of the user's body is a state suitable for sleep is determined, and the user's body is able to be put into a state suitable for sleep.

According to the present preferred embodiment, in particular, the threshold value used to determine whether the state of the user's body is a state suitable for sleep is set to become smaller as the heartbeat interval becomes longer. That is, since the threshold value (see the broken line in FIG. 4) is set in accordance with the combination of the pulse wave transit time and the heartbeat interval, whether the state of the user's body is a state suitable for sleep is able to be more accurately determined.

According to the present preferred embodiment, the threshold value is set based on the maximum value of the pulse wave transit time during sleep or the pulse wave transit time immediately before the user wakes up, that is, the pulse wave transit time that has not been reduced by daytime activities. Therefore, the threshold value used to determine whether the state has become a state suitable for sleep is able to be appropriately set.

According to the present preferred embodiment, the temperature of the forearms, i.e., the wrists in the present preferred embodiment, is increased when the user's body has not reached a state suitable for sleep. In doing so, only the forearms can be heated without increasing the temperature of the trunk. Therefore, the state becomes such that the forearms are heated to dilate the peripheral vessels of the fingers, but the temperature of the trunk is relatively low, which is thus a state suitable for sleep. As a result, the user is able to easily fall asleep and sleep well.

According to the present preferred embodiment, the temperature of the legs is increased when the user's body has not reached a state suitable for sleep. In doing so, only the legs can be heated without increasing the temperature of the trunk. Therefore, the state becomes such that the legs are heated to dilate the peripheral vessels of the feet, but the temperature of the trunk is relatively low, which is thus a state suitable for sleep. As a result, the user is able to easily fall asleep and sleep well.

Furthermore, according to the present preferred embodiment, the temperature of the neck is reduced when it is determined that the user's body has not reached a state suitable for sleep. In doing so, the temperature of blood flowing to the head is lowered, thus reducing the temperature of the head and putting the user's body into a state suitable for sleep. As a result, the user is able to easily fall asleep and sleep well.

In a preferred embodiment of the present invention, preferably, an electrocardiographic signal and a photoelectric pulse wave signal are detected, a pulse wave transit time is measured from a time difference between the R-wave peak of the detected electrocardiographic signal and the peak of the detected photoelectric pulse wave signal, and whether the state of the user's body is a state suitable for sleep is determined based on the measured pulse wave transit time. Alternatively, a photoelectric pulse wave signal may be detected at two points on the body, a pulse wave transit time may be measured from a peak time difference between the two detected photoelectric pulse wave signals (a first photoelectric pulse wave signal and a second photoelectric pulse wave signal), and whether the state of the user's body is a state suitable for sleep may be determined based on the measured pulse wave transit time.

Figure 7:
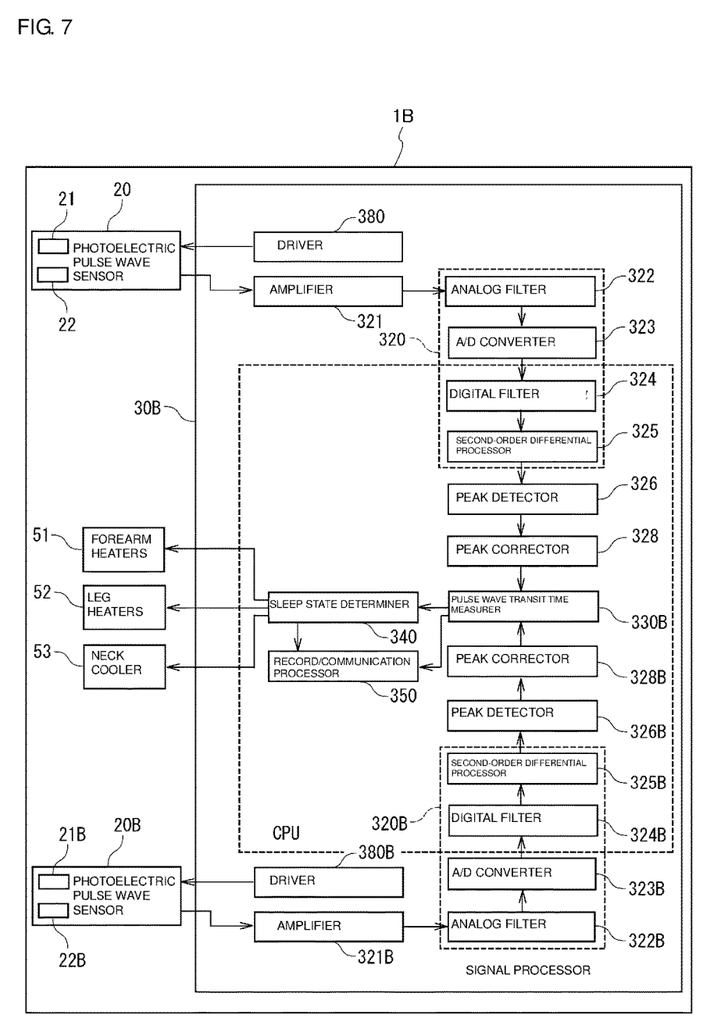
FIG. 7 is a block diagram illustrating the configuration of a sleep support apparatus according to a modification of a preferred embodiment of the present invention.

Next, using FIG. 7, the configuration of a sleep support apparatus 1B according to a modification of a preferred embodiment of the present invention will be described. Descriptions of configurations that are the same as or similar to those in the sleep support apparatus 1 according to the above-described preferred embodiment are simplified or omitted, and different points will be primarily described. FIG. 7 is a block diagram illustrating the configuration of the sleep support apparatus 1B according to the modification. In FIG. 7, elements that are the same as or similar to those of the sleep support apparatus 1 are denoted by the same symbols.

The sleep support apparatus 1B is different from the sleep support apparatus 1 in the following points: the sleep support apparatus 1B includes a photoelectric pulse wave sensor 20B (corresponding to a second pulse wave sensor described in the claims) that detects a photoelectric pulse wave signal, instead of the pair of electrocardiographic electrodes (the first electrocardiographic electrode 11 and the second electrocardiographic electrode 12) that detect an electrocardiographic signal; and the sleep support apparatus 1B includes a signal processor 30B that measures a pulse wave transit time from a detected first photoelectric pulse wave signal and a detected second photoelectric pulse wave signal and determines whether the body state is a state suitable for sleep, instead of the signal processor 30, which measures a pulse wave transit time from the detected electrocardiographic signal and photoelectric pulse wave signal and determines whether the body state is a state suitable for sleep.

The signal processor 30B is different from the signal processor 30 in that the signal processor 30B preferably includes an amplifier 321B, an analog filter 322B, an A/D converter 323B, a digital filter 324B, a second-order differential processor 325B, a peak detector 326B, a peak corrector 328B, and a pulse wave transit time clock 330B, instead of the amplifier 311, the analog filter 312, the A/D converter 313, the digital filter 314, the peak detector 316, the peak corrector 318, and the pulse wave transit time clock 330 described above. The other configurations are the same as or similar to those of the above-described sleep support apparatus 1, and detailed descriptions thereof are omitted here.

The photoelectric pulse wave sensor 20B is the same or substantially the same as the above-described photoelectric pulse wave sensor 20 (corresponding to a first pulse wave sensor described in the claims), and a detailed description thereof will be omitted here. Preferably, the photoelectric pulse wave sensor 20 and the photoelectric pulse wave sensor 20B are arranged on, for example, the neck and a wrist, an upper arm and a wrist, a wrist and a finger, or a thigh and an ankle, for example.

Since the amplifier 321B, the analog filter 322B, the A/D converter 323B, the digital filter 324B, the second-order differential processor 325B, the peak detector 326B, and the peak corrector 328B are the same as the amplifier 321, the analog filter 322, the A/D converter 323, the digital filter 324, the second-order differential processor 325, the peak detector 326, and the peak corrector 328 described above, detailed descriptions thereof will be omitted here. When it is determined that the delay time of the first photoelectric pulse wave signal is the same or substantially the same as the delay time of the second photoelectric pulse wave signal, it is not essential to provide the peak correctors 328 and 328B, and the peak corrector 328 and 328B may be omitted.

The pulse wave transit time clock 330B obtains the pulse wave transit time from the time difference between the peak of the first photoelectric pulse wave signal, detected by the peak detector 326 and corrected by the peak corrector 328, and the peak of the second photoelectric pulse wave signal, detected by the peak detector 326B and corrected by the peak corrector 328B. That is, the pulse wave transit time clock 330B functions as pulse wave transit time computer recited in the claims.

Note that the pulse wave transit time clock 330B calculates the pulse rate, pulse interval, and other parameters from the photoelectric pulse wave signal, in addition to the pulse wave transit time. That is, the pulse wave transit time clock 330B also functions as the pulse interval calculator recited in the claims. Measurement data, such as the calculated pulse wave transit time, pulse rate, pulse interval, and acceleration pulse wave, are output to the sleep state detector 340 and the record/communication processor 350.

The sleep state detector 340 determines that the user's body has not reached a state suitable for sleep when the pulse wave transit time obtained by the pulse wave transit time clock 330B is less than or equal to a threshold value. The threshold value is set to be smaller when the pulse interval becomes longer. Therefore, the sleep state detector 340 determines that the user's body has not reached a state suitable for sleep when the pulse wave transit time is less than or equal to a threshold value corresponding to the pulse interval, that is, when the combination of the pulse interval and the pulse wave transit time is not in an area suitable for sleep. Alternatively, the sleep state detector 340 may determine that the user's body has not reached a state suitable for sleep when the pulse wave transit time is less than or equal to a constant threshold value, regardless of the pulse interval.

According to the modification of a preferred embodiment of the present invention described above, the pulse wave transit time is obtained from the time difference between the peak of the first photoelectric pulse wave signal and the peak of the second photoelectric pulse wave signal, and it is determined that the user's body has not reached a state suitable for sleep when the pulse wave transit time is less than or equal to the threshold value. Accordingly, whether the state of the user's body is a state suitable for sleep can be effectively determined, and the user's body is able to be put into a state suitable for sleep.

Although preferred embodiments of the present invention have been described above, the present invention is not limited to the above-described preferred embodiments, and various modifications are possible. For example, although the photoelectric pulse wave sensor is used to obtain a pulse wave signal in a preferred embodiment, another pulse wave sensor, such as a piezoelectric pulse wave sensor may be used, instead of the photoelectric pulse wave sensor.

Alternatively, data, such as the pulse wave transit time, the heartbeat interval, the pulse interval, the measurement time, and the sleep state determination result, may be saved in the record/communication processor 350, and may be read out as a daily modification history. These items of data may be wirelessly transmitted via the record/communication processor 350 to an external device, such as a smartphone, instead of being saved in the apparatus. Alternatively, the data may be saved in the record/communication processor 350 while the data is being measured, and, after the measurement ends, an external device may be coupled to the apparatus and the data may be automatically transmitted to the external device.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

What is claimed is:

1. A sleep support apparatus comprising:
a pair of electrocardiographic electrodes that detect an electrocardiographic signal; a pulse wave sensor that detects a pulse wave signal;
a peak detector that detects a peak of the electrocardiographic signal, detected by the pair of electrocardiographic electrodes, and of the pulse wave signal, detected by the pulse wave sensor;
a pulse wave transit time computer that obtains a pulse wave transit time from a time difference between the peak of the pulse wave signal and the peak of the electrocardiographic signal, the peaks being detected by the peak detector; and
a detector configured to determine that a user's body has not reached a state suitable for sleep using the pulse wave transit time, wherein a state not suitable for sleep is when the pulse wave transit time obtained by the pulse wave transit time computer is less than or equal to a threshold value.

2. The sleep support apparatus according to claim 1, further comprising:
a heartbeat interval calculator that obtains a heartbeat interval from the electrocardiographic signal detected by the pair of electrocardiographic electrodes; wherein
the threshold value is set to become smaller as the heartbeat interval becomes longer; and
the detector determines that the user's body has not reached a state suitable for sleep when the pulse wave transit time is less than or equal to another threshold value corresponding to the heartbeat interval obtained by the heartbeat interval calculator.

3. The sleep support apparatus according to claim 1, wherein the threshold value is set using a maximum value of the pulse wave transit time during sleep.

4. The sleep support apparatus according to claim 1, wherein the pulse wave sensor is a photoelectric pulse wave sensor that includes a light emitter and a light receiver, and that detects a photoelectric pulse wave signal.

5. The sleep support apparatus according to claim 1, further comprising a forearm heater that increases a temperature of a forearm when the detector determines that the user's body has not reached the state suitable for sleep.

6. The sleep support apparatus according to claim 5, wherein the forearm heater has a shape of a wristband.

7. The sleep support apparatus according to claim 1, further comprising a leg heater that increases a temperature of a leg when the detector determines that the user's body has not reached the state suitable for sleep.

8. The sleep support apparatus according to claim 1, further comprising a neck cooler that reduces a temperature of a neck when the detector determines that the user's body has not reached the state suitable for sleep.

9. A sleep support apparatus comprising:
a first pulse wave sensor and a second pulse wave sensor that detect a pulse wave signal;
a peak detector that detects a peak of a first pulse wave signal, detected by the first pulse wave sensor, and of a second pulse wave signal, detected by the second pulse wave sensor;

a pulse wave transit time computer that obtains a pulse wave transit time from a time difference between the peak of the first pulse wave signal and the peak of the second pulse wave signal, the peaks being detected by the peak detector; and a detector configured to determine that a user's body has not reached a state suitable for sleep using the pulse wave transit time, wherein a state not suitable for sleep is when the pulse wave transit time obtained by the pulse wave transit time computer is less than or equal to a threshold value.

10. The sleep support apparatus according to claim 9, further comprising:

a pulse interval calculator that obtains a pulse interval from the first pulse wave signal or the second pulse wave signal; wherein the threshold value is set to become smaller as the pulse interval becomes longer; and the detector determines that the user's body has not reached a state suitable for sleep when the pulse wave transit time is less than or equal to another threshold value corresponding to the pulse interval obtained by the pulse interval calculator.

11. The sleep support apparatus according to claim 9, wherein the threshold value is set using a maximum value of the pulse wave transit time during sleep.

12. The sleep support apparatus according to claim 9, wherein the first pulse wave sensor and the second pulse wave sensor are photoelectric pulse wave sensors, each of which includes a light emitter and a light receiver, and detects a photoelectric pulse wave signal.

13. The sleep support apparatus according to claim 9, further comprising a forearm heater that increases a temperature of a forearm when the detector determines that the user's body has not reached the state suitable for sleep.

14. The sleep support apparatus according to claim 13, wherein the forearm heater has a shape of a wristband.

15. The sleep support apparatus according to claim 9, further comprising a leg heater that increases a temperature of a leg when the detector determines that the user's body has not reached the state suitable for sleep.

16. The sleep support apparatus according to claim 9, further comprising a neck cooler that reduces a temperature of a neck when the detector determines that the user's body has not reached the state suitable for sleep.

* * * * *